(12) United States Patent
Le Neel et al.

(10) Patent No.: US 9,437,798 B2
(45) Date of Patent: Sep. 6, 2016

(54) COMBO BIO AND TEMPERATURE DISPOSABLE SENSOR ON FLEXIBLE FOIL

(71) Applicant: STMicroelectronics Pte Ltd., Singapore (SG)

(72) Inventors: Olivier Le Neel, Singapore (SG); Suman Cherian, Singapore (SG); Calvin Leung, Singpaore (SG); Ravi Shankar, Singapore (SG); Tien Choy Loh, Singapore (SG); Shian Yeu Kam, Singapore (SG)

(73) Assignee: STMICROELECTRONICS PTE LTD., Singapore (SG)

( * ) Notice: Subject to any disclaimer, the term of this patent is extended or adjusted under 35 U.S.C. 154(b) by 553 days.

(21) Appl. No.: 13/929,525

(22) Filed: Jun. 27, 2013

(65) Prior Publication Data

US 2015/0001075 A1 Jan. 1, 2015

(51) Int. Cl.
*G01N 27/327* (2006.01)
*H01L 35/34* (2006.01)

(52) U.S. Cl.
CPC ........... *H01L 35/34* (2013.01); *G01N 27/3274* (2013.01); *Y10T 29/49117* (2015.01)

(58) Field of Classification Search
None
See application file for complete search history.

(56) References Cited

U.S. PATENT DOCUMENTS

| | | |
|---|---|---|
| 5,391,250 A | 2/1995 | Cheney, II et al. |
| 8,617,381 B2 | 12/2013 | Sun et al. |
| 2009/0000947 A1 | 1/2009 | Akahori et al. |
| 2012/0165635 A1 | 6/2012 | Radhakrishnan et al. |
| 2012/0168882 A1 | 7/2012 | Cherian et al. |
| 2013/0010826 A1 | 1/2013 | Le Neel et al. |
| 2013/0168815 A1 | 7/2013 | Le Neel et al. |
| 2015/0001071 A1 | 1/2015 | Le Neel et al. |

OTHER PUBLICATIONS

Zhu et al., "Planar Amperometric Glucose Sensor Based on Glucose Oxidase Immobilized by Chitosan Film on Prussian Blue Layer." ISSN 1424-8220, Sensors 2002, 2, pp. 127-136 (10 pages).

*Primary Examiner* — J. Christopher Ball
(74) *Attorney, Agent, or Firm* — Seed IP Law Group PLLC

(57) ABSTRACT

A bio-fluid sensor is formed by depositing polyimide on a glass substrate. Gold and platinum are deposited on the polyimide and patterned to form fluid sensing electrodes, signal traces, and a temperature sensor. The fluid sensor is then fixed to a flexible tape and peeled off of the glass substrate.

20 Claims, 13 Drawing Sheets

COMBO BIO AND TEMPERATURE DISPOSABLE SENSOR ON FLEXIBLE FOIL

BACKGROUND

1. Technical Field

The present disclosure relates to the field of fluid sensors. The present disclosure relates more particularly to the field of disposable biosensor test strips.

2. Description of the Related Art

Biosensors are devices that utilize biological reactions to identify analyte species such as glucose, proteins, hormones, nucleotides etc. Some biosensors are designed to output a current indicative of the presence of the analyte to be detected. As the size of the biosensors scales downward in order to reduce costs of manufacturing biosensors, the dimensions of the sensing area also decrease. Due to this, the measured current signal due to electrochemical reactions is also decreased to the range of nano-amperes (nA) or even pico-amperes (pA).

Highly sensitive measurements are needed to obtain accurate and reproducible signals especially for the detection of low and ultralow concentrations of species such as C-reactive proteins. For highly sensitive, high-performance biosensors, the measuring conditions need to be carefully monitored to ensure accuracy measurements.

BRIEF SUMMARY

One embodiment is a fluid test strip for testing the presence or concentration of a particular analyte within a fluid. The fluid test strip includes a substrate and a dielectric material on the substrate. Sensing electrodes are positioned on the dielectric material in a fluid receiving area. Contact pads are also positioned on the dielectric material. Conductive signal traces connect the detection electrodes to respective contact pads. A reactive enzyme is positioned on the dielectric material and on the sensing electrodes in the fluid receiving area. A temperature sensing element is also positioned on the dielectric material in the fluid receiving area. The temperature sensing element is also connected to two or more of the contact pads by a signal trace.

The fluid test strip is configured to be coupled to a fluid test strip reader. The fluid test strip reader applies respective voltages to the electrodes via the contact pads. When the fluid to be tested is placed in the fluid receiving area of the test strip, a chemical reaction occurs between the enzyme and the fluid. The strength of the chemical reaction is dependent upon concentration of the analyte in the fluid. A current passes between the electrodes through the reactive enzyme. The magnitude of the current corresponds to the strength of the chemical reaction. The fluid test strip reader measures this current to provide an indication of the concentration of the analyte in the fluid. The fluid test strip reader also passes a current through the temperature sensing element to obtain an indication of the temperature of the fluid. The fluid test strip reader measures the concentration of the analyte based on the current in the temperature sensing element and the current between the electrodes. Because the reaction rate between the enzyme and the analyte is also temperature dependent, obtaining a measurement of the temperature of the fluid provides a more accurate measurement of the concentration of the analyte in the fluid.

One embodiment is a method for making a fluid test strip. The method includes depositing a first dielectric material on a flat substrate and opening apertures in the dielectric material. A first conductive material is deposited on the first dielectric material and on the flat substrate in the apertures. The first conductive material is patterned to form fluid sensing electrodes and contact pads in respective apertures. The patterning of the first conductive material also defines conductive signal traces of the first conductive material on the first dielectric material electrically connecting the electrodes to respective contact pads. A second conductive material is deposited on the first conductive material and on the first dielectric material. The second conductive material is patterned to define a temperature sensing element adjacent to but electrically isolated from the electrodes. The temperature sensing element is electrically connected to two or more of the contact pads by two or more of the conductive traces. A second dielectric material is deposited on the first dielectric material and on the first and second conductive materials. An adhesive tape is then placed on the second dielectric material and the test strip is flipped so that the flat substrate is on top of the device. The flat substrate is then peeled away from the surface of the first dielectric material, the electrodes, and the contact pads. This leaves a fluid test strip having the electrodes and contact pads having a surface that is planar with the top surface of the first dielectric material. The reactive enzyme is then placed on the electrodes and the first dielectric material in a fluid receiving area of the fluid test strip.

DETAILED DESCRIPTION

Figure 1:
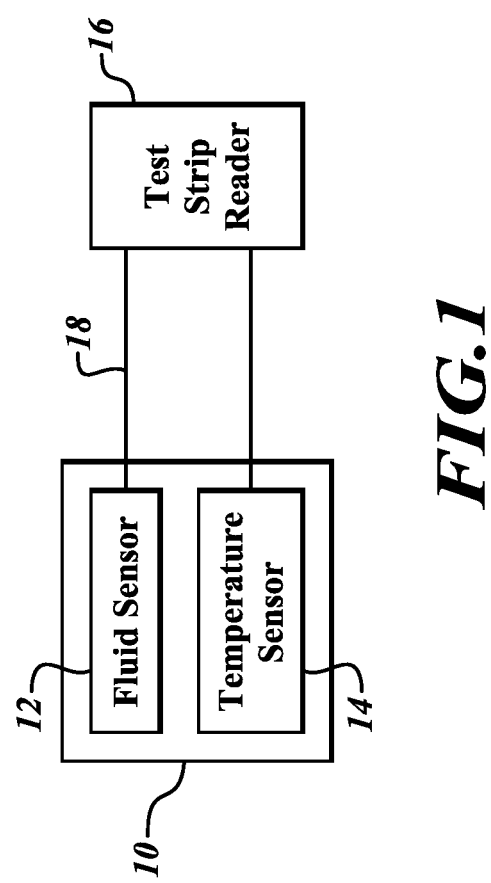
FIG. 1 is a block diagram of a fluid test strip and a fluid test strip reading device according to one embodiment.

FIG. 1 is a block diagram of a fluid sensing system including a fluid test strip 10 communicatively coupled to a fluid test strip reader 16. The fluid test strip 10 includes a fluid sensor 12, a temperature sensor 14, and communication lines 18 for electrically connecting with the fluid test strip reader 16.

The fluid test strip 10 and fluid test strip reader 16 are configured to measure the concentration or merely detect the presence of an analyte in a fluid that is placed on the fluid sensor 12 of the fluid test strip 10. The fluid test strip 10 and the fluid test strip reader 16 function by coupling the fluid test strip 10 to the fluid test strip reader 16 and placing the fluid to be tested on the fluid sensor 12 of the fluid test strip 10. The fluid test strip reader 16 supplies a voltage to the fluid sensor 12 via the communication lines 18. The fluid sensor 12 passes a sensor signal back to the fluid test strip reader 16 indicative of the concentration of the analyte in the fluid.

In some instances the magnitude of the sensor signal can be affected by both the concentration of the analyte and the temperature of the fluid. For this reason the fluid test strip 10 includes the temperature sensor 14. The temperature sensor 14 provides a temperature signal to the fluid test strip reader 16. The fluid test strip reader 16 outputs a measurement of the concentration of the analyte in the fluid based on both the sensor signal and the temperature signal. In this way, the fluid test strip reader 16 can output an accurate measurement of the concentration of the analyte in the fluid by taking into consideration the temperature of the fluid.

In one example, the fluid test strip 10 is a blood glucose test strip. The blood glucose test strip measures the concentration of glucose in a patient's blood. By placing the blood glucose test strip into the test strip reader 16, and by placing a small amount of the patient's blood on the test strip, the test strip reader 16 can provide a measurement of the concentration of glucose in the patient's blood.

The blood glucose test strip includes a fluid receiving area on which the small amount of the patient's blood is placed for testing. The fluid sensor 12 comprises electrodes located in the fluid receiving area of the fluid test strip 10. The blood glucose test strip includes a reactive enzyme, such as glucose oxidase, on the electrodes in the fluid receiving area. When blood is placed on the reactive enzyme in the fluid receiving area, the enzyme reacts with the glucose in the blood causing current to flow between the electrodes. The reaction between the enzyme and the glucose becomes stronger as the concentration of glucose increases. The current flowing between the electrodes increases as the reaction become stronger. The magnitude of the current flowing between the electrodes is indicative of the concentration of glucose in the blood.

However, the strength of the reaction between the glucose and the enzyme is also dependent on temperature. For a given concentration of glucose in the patient's blood, the reaction between the enzyme in the glucose is different for different temperatures. Even if the temperature of the blood changes by a very small amount, the measurement of glucose in the blood can be affected significantly. Having an accurate measurement of the temperature of the fluid can help ensure an accurate measurement of the concentration of glucose in the blood.

In one example, the temperature sensor 14 is a temperature sensing resistor placed in the fluid receiving area of the test strip 10. The temperature sensing resistor is formed of a material having a constant temperature coefficient of resistance (TCR) over the range of likely fluid temperatures. In other words the resistance of the temperature sensing resistor changes linearly with changes in temperature over a range of probable temperatures of the fluid. In the case of a blood glucose test strip, the temperature of the fluid is likely to be within a few degrees of 37° C., the normal body temperature of a healthy individual. Thus, for a blood glucose sensor, it is beneficial for the temperature coefficient of resistance of the temperature sensing resistor to be constant for a small range of temperatures around 37° C. For other types of fluid test strips 10, the range of possible temperatures may be much larger.

In one example, the temperature sensing resistor is made of platinum. Platinum has a relatively constant TCR of about 3850 ppm/° C. over a wide range of temperatures. The resistance of the platinum temperature sensing resistor provides a reliable indication of the temperature of the fluid. This indication of the temperature of the fluid can in turn be used to calculate an accurate value of the concentration of the analyte in the fluid.

While a blood glucose sensor has been described as one example of a fluid test strip 10, many other embodiments are possible. For example, the fluid test strip 10 can be a protein sensor, a hormone sensor, a nucleotide sensor, or large number of other types of sensors.

Figure 2:
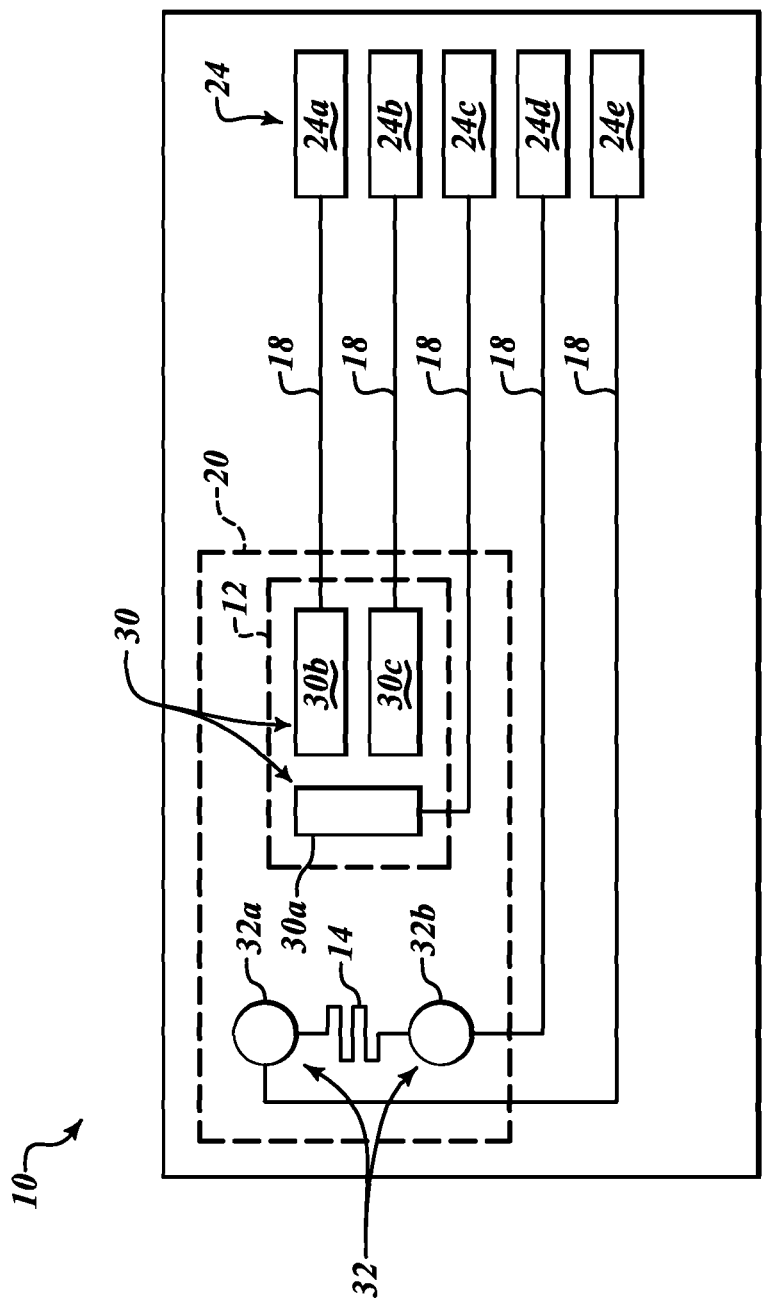
FIG. 2 is a top view of a fluid test strip according to one embodiment.

FIG. 2 is a simplified schematic of a fluid test strip 10 according to one embodiment. The fluid test strip 10 includes a fluid receiving area 20. Sensor electrodes 30, labeled here individually as 30a, 30b, and 30c, are positioned in the fluid receiving area 20. The temperature sensing resistor 14 is also positioned in the fluid receiving area 20. Thermal connectors 32, labeled here individually as 32a and 32b, are also positioned in the fluid receiving area 20 and are electrically coupled on opposing ends of the temperature sensing resistor 14. Contact pads 24, here labeled individually as 24a-24e are connected by signal lines 18 to the sensing electrodes 30a, 30b, 30c and the temperature sensing resistor 14.

The fluid test strip 10 is configured to output at the contact pads 24a-24e an indication of both the concentration of an analyte in the fluid and the temperature of the fluid. This is accomplished by placing the fluid test strip 10 in a fluid test strip reader 16 as described with relation to FIG. 1, and placing a small amount of the fluid on the fluid receiving area 20. The fluid test strip reader 16 applies test voltages to the contact pads 24a-24e and reads signals from the contact pads 24a-24e and computes a value of the concentration of the analyte in the fluid.

In one example, the fluid test strip reader 16 obtains an indication of the concentration of the analyte from the fluid test strip 10 by applying a voltage, for example 5 V, between contact pads 24a and 24b. The analyte in the fluid reacts with an enzyme covering the fluid receiving area. The reaction between the analyte and the enzyme enables a sensor current to flow between electrodes 30b and 30c. The magnitude of the sensor current depends on the strength of the reaction between the enzyme in the analyte. The strength of the reaction between the enzyme in the analyte depends on the concentration of the analyte in the fluid. The sensor current therefore provides an indication of the concentration of the analyte in the fluid.

The fluid test strip reader 16 obtains an indication of the temperature of the fluid by applying a voltage, for example 5 V, between contact pads 24d and 24e. The voltage applied across the temperature sensing resistor 14 causes a temperature current to flow through the temperature sensing resistor 14. The temperature current flowing across the resistor 14 is dependent on the voltage across the resistor 14 divided by the resistance of the resistor 14. Because the resistance of the temperature sensing resistor 14 changes linearly with changes in temperature, the temperature current flowing through the temperature sensing resistor 14 provides an indication of the temperature of the fluid. The fluid test strip reader 16 therefore measures the current flowing between contact pads 24d and 24e.

The thermal connectors 32a and 32b conduct heat from the fluid to the temperature sensing resistor 14 to ensure that the temperature sensing resistor 14 is the same temperature as the fluid. The thermal connectors 32a and 32b are positioned on the surface of the fluid test strip 10 in the fluid receiving area 20. The temperature sensing resistor 14 is positioned below the top surface of the fluid test strip 10 under a layer of dielectric material. Thus, in the absence of the thermal connectors 32a and 32b, the temperature sensing resistor 14 could be thermally isolated from the fluid and could therefore be at a different temperature than the fluid. The thermal connectors 32a and 32b are made from a material that is highly thermally conductive. When the fluid is placed on the fluid test strip 10, the thermal connectors 32a and 32b are in thermal contact with the fluid and quickly arrive at the same temperature as the fluid. The thermal conductors 32a and 32b are thermally connected to the temperature sensing resistor 14, and heat to the temperature sensing resistor 14 also arrives very quickly at the same temperature as the fluid. The thermal conductors 32a and 32b therefore help to ensure that the temperature sensing resistor 14 provides an accurate indication of the temperature of the fluid.

In one example, the electrodes 32a-32c and contact pads 24a-24e each have a surface area of about 250 µm. The thermal conductors 32a and 32b each have a surface area of about 100 µm. The fluid receiving area is for example about 1 mm×2 mm. The length of the electrical connectors 18 is about 1 cm. Thus, the fluid receiving area makes up a relatively small portion of the surface area of the fluid test strip 10, while the great majority of the surface area of the fluid test strip 10 is in the space separating the fluid receiving area from the contact pads 24a-24e.

In one embodiment the electrodes 30a-30c, the contact pads 24a-24e, and the thermal conductors 32a and 32b are all made of gold. The temperature sensing resistor 14 is made of platinum and has a resistance of about 1 kΩ.

As described previously in relation to FIG. 1, the fluid test strip can be a blood glucose sensor, a protein sensor, a nucleotide sensor, hormone sensor, or many other types of sensors. The specific materials, dimensions, and physical characteristics such as resistance given above are provided only by way of example. Those of skill in the art will understand that the contact pads 24a-24e, the electrodes 30a-30c, and the thermal conductors 32a and 32b can be made of materials other than gold, for example copper, aluminum, alloys of these metals, or any other suitable conductive materials.

Figure 3A:
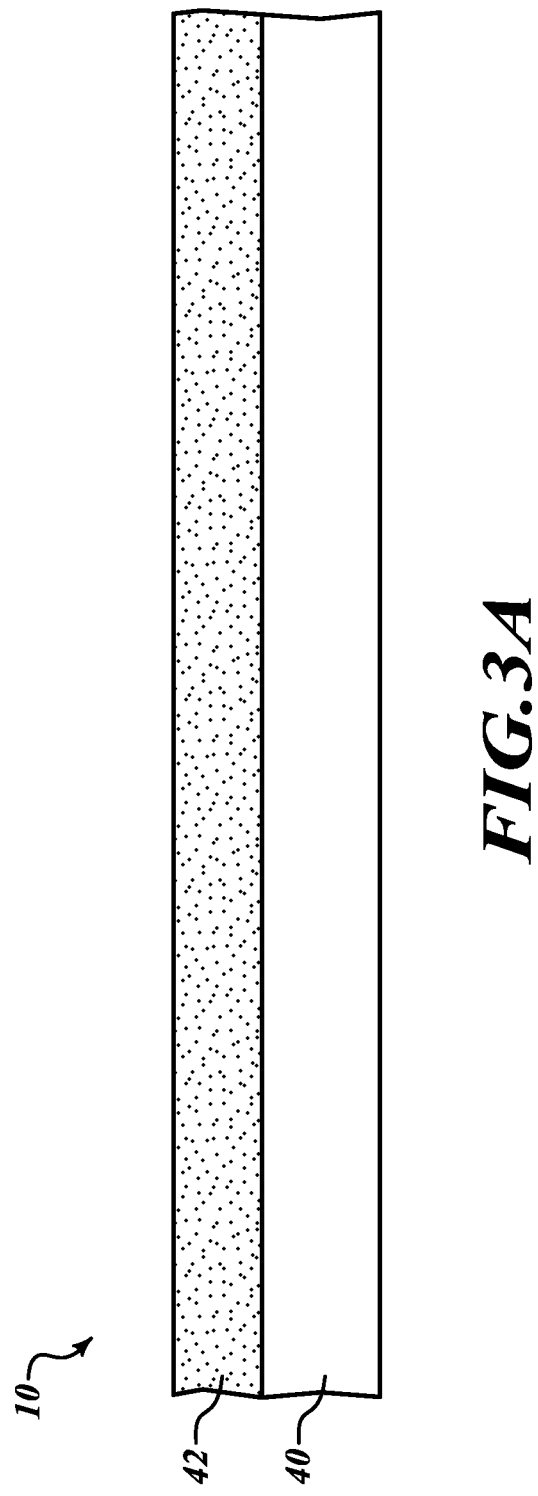
FIGS. 3A-3G are cross sections of a fluid test strip during successive process steps for forming the fluid test strip according to one embodiment.

FIG. 3A is a cross section of a fluid test strip 10 at an early stage of manufacture according to one embodiment. Manufacture of the fluid test strip 10 is begun by depositing a first layer of dielectric material 42 on a substrate 40. The first layer of dielectric material 42 is, for example, a non-photosensitive polyimide 1. The polyimide can be deposited in liquid form on the substrate 40 and spun to achieve a thickness of about 10 µm. After the polyimide has been spun, it is cured so that it hardens on the substrate 40.

The substrate 40 is for example glass and is 750 µm thick. Materials other than polyimide and glass can be used for the first layer of dielectric material 42 and the substrate 40. However it is desirable that the particular materials of the substrate 40 and the first layer of dielectric material 42 are selected such that the substrate 40 can be peeled away from the first layer of dielectric material 42 in a subsequent step as described further below.

Figure 3B:
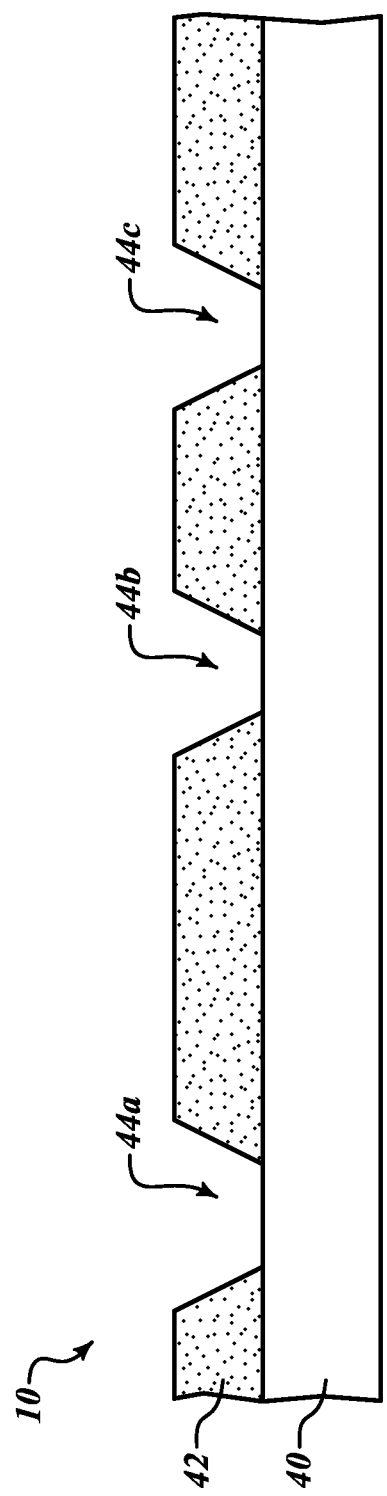

In FIG. 3B, apertures 44a, 44b, and 44c are open in the first layer of dielectric material 42 to expose the substrate 40 below. The apertures 44a, 44b, and 44c are opened by utilizing conventional photolithography steps. For example, photoresist is formed of the first layer of dielectric material 42 and patterned to exposed portions of the first layer of dielectric material 42. An etch step is then performed whereby the exposed portions of the dielectric material 42 are etched leaving apertures 44a, 44b, and 44c in the first layer of dielectric material 42.

Figure 3C:
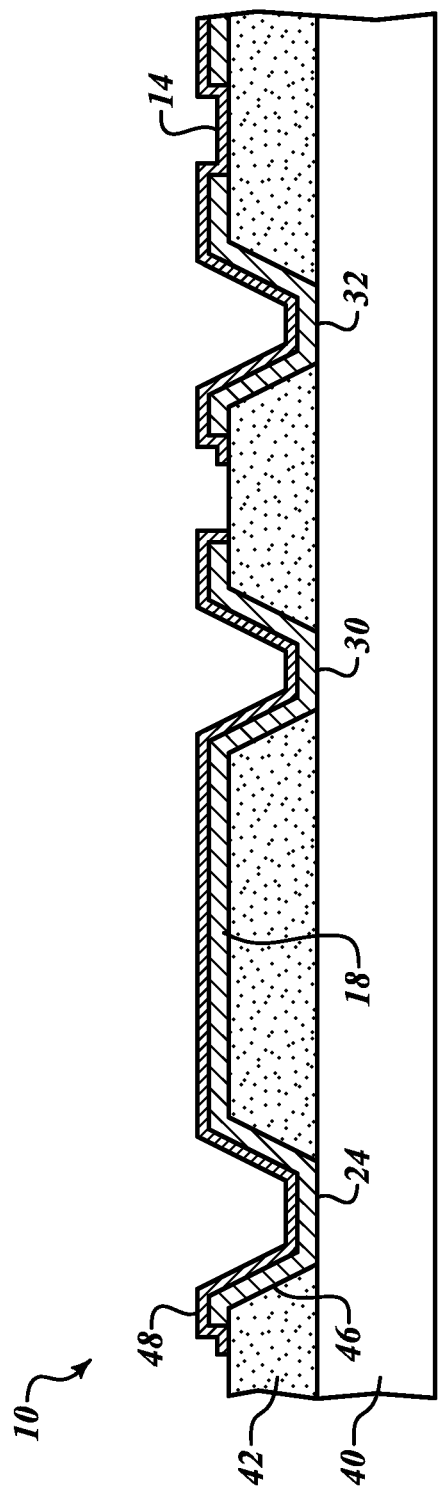

In FIG. 3C, a first layer of conductive material 46 is deposited on the first layer of dielectric material 42 and in the apertures 44a, 44b, and 44c. A portion of the first layer of conductive material 46 is therefore in contact with the substrate 40 in the apertures 44a, 44b, and 44c. The first layer of conductive material 46 is, in one example, gold having a thickness of about 500 nm. The first layer of conductive material 46 can be deposited by physical vapor deposition (PVD), for example by sputtering, to achieve a thin layer with good step coverage in the apertures 44a, 44b, and 44c. The first layer of conductive material 46 is then patterned and etched using conventional photolithography methods as described above. The portions of the first layer of conductive material 46 in the apertures 44a, 44b, and 44c in contact with the substrate 40 correspond to the contact pads 24a-24e, the electrodes 30a-30c, and the thermal conductors 32a-32b of FIG. 2. In FIG. 3C, due to the nature of the cross section, only one contact pad 24, one electrode 30, and one thermal conductor 32 are shown. The portion 18 of the first layer of conductive material 46 on top of the first layer of dielectric material 42 electrically connecting the contact pad 24 and the electrode 30 corresponds to one of the conductive lines 18 of FIGS. 1 and 2. The first layer of conductive material 46 can be conductive material other than gold, such as aluminum, copper, or another suitable conductive material with the stipulation that the particular materials of the layer 46 and the substrate 40 be such that the substrate 40 can be peeled away from the contact pad 24, electrode 30, and the thermal conductor 32 without damaging them, as will be explained further below.

A second layer of conductive material 48 is also deposited on the first layer of conductive material 46 and on the first layer of dielectric material 42. In one example the second layer of conductive material 48 is platinum. The second layer of conductive material 48 can be deposited by physical vapor deposition, and has a thickness of about 15 nm. The second layer of conductive material 48 is also patterned and etched using conventional photolithographic methods. In general, the second layer of conductive material 48 remains wherever the first layer of conductive material 46 remains. However the second layer of conductive material 48 forms a temperature sensing resistor 14 of the fluid test strip 10. The portion of the second layer of conductive material 48 that forms the temperature sensing resistor 14 remains on the first layer of dielectric material 42. Though not shown in FIG. 3C, the temperature sensing resistor 14 is electrically coupled to two contact pads by two conductive lines 18.

Figure 3D:
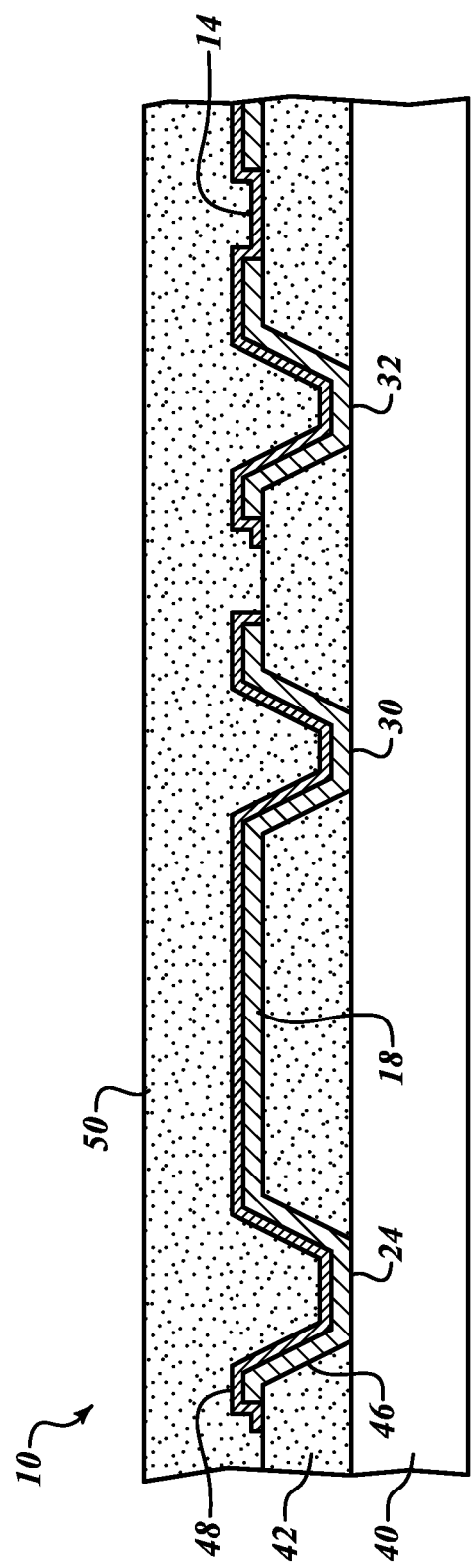

In FIG. 3D a second layer of dielectric material 50 is deposited on the first layer of dielectric material 42 and the second layer of conductive material 48. The second layer of dielectric material 50 is for example polyimide. The second layer of dielectric material 50 can be deposited in liquid form and spun, as described previously, to form a layer about 10 µm thick. The second layer of dielectric material 50 is then hardened by curing.

Figure 3E:
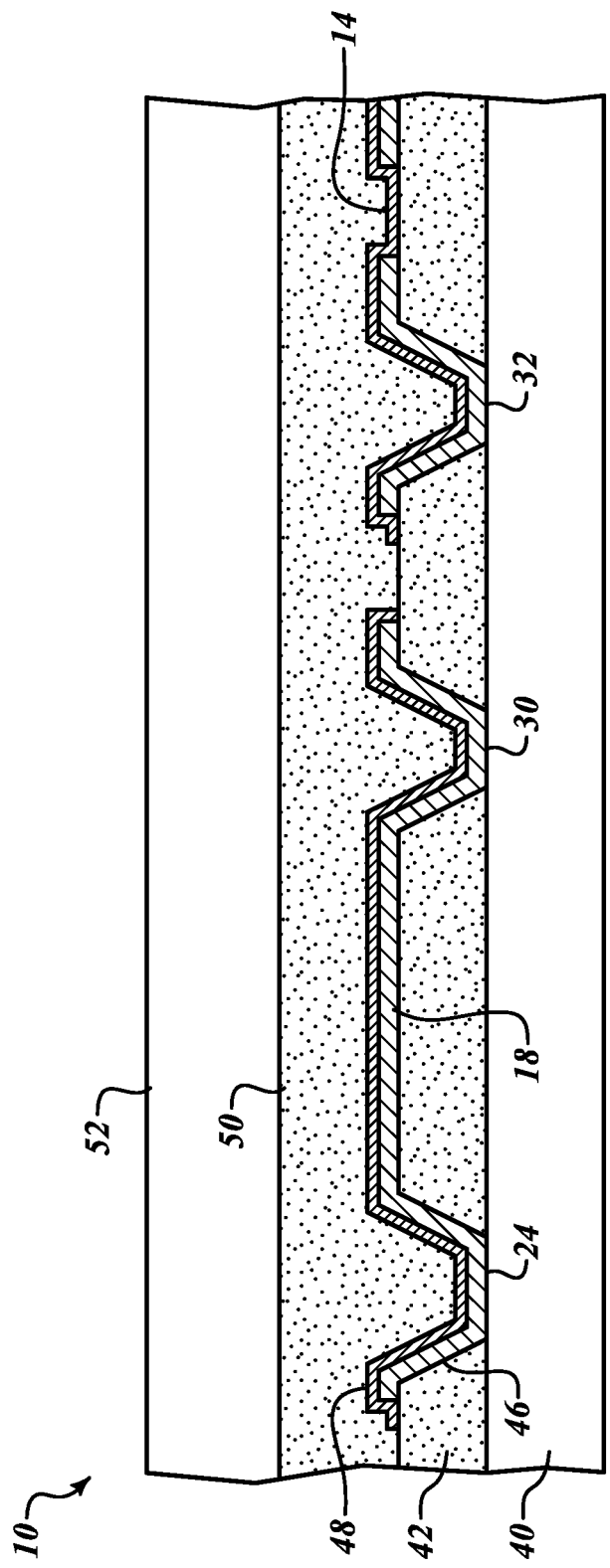

In FIG. 3E an adhesive dielectric layer 52 is deposited on the second layer of dielectric material 50. The adhesive dielectric layer 52 is for example a layer of tape which is adhered to the second layer of dielectric material 50. The adhesive dielectric layer 52 is about 150 µm thick and is strongly adhesive to the second layer of dielectric material 52.

Figure 3F:
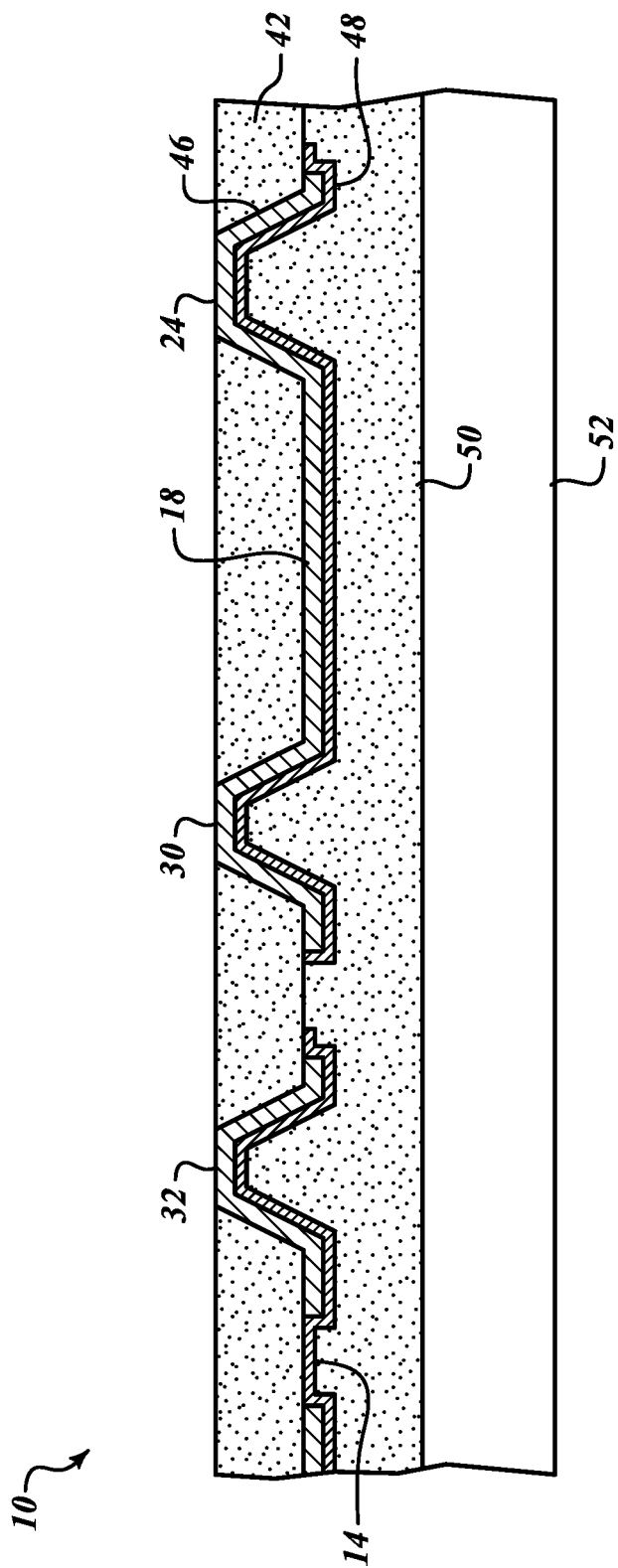
Figure 3G:
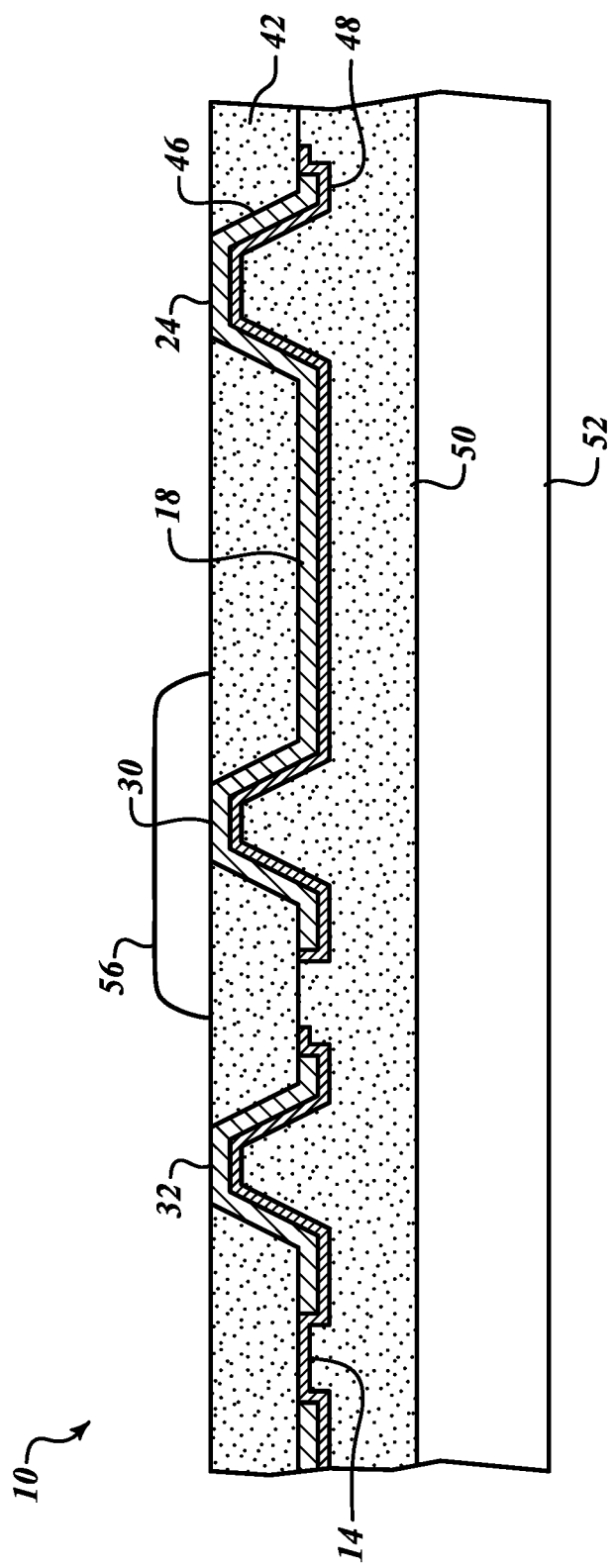

In FIG. 3F, the fluid test strip 10 has been flipped over and the substrate 40 has been peeled away. The contact pad 24, the electrode 30, and the thermal conductor 32 are now exposed on the top layer of the fluid test strip 10. The surface of the first layer of dielectric material 42 that was once coupled to the substrate 40 is now the top surface of the fluid test strip 10. Because both the first layer of dielectric material 42 and the first layer of conductive material 46 were on the planar surface of the substrate 40, the first layer of dielectric material 42, the contact pad 24, electrode 30, and the thermal conductor 32 share a planar top surface.

In FIG. 3D an enzyme 56 has been deposited on top of the electrode 30. The particular material of the enzyme 56 depends on the analyte to be detected by the fluid test strip 10. In the example of a blood glucose test strip, the enzyme 56 is glucose oxidase. Once blood is placed on the glucose oxidase, a chemical reaction occurs between the glucose oxidase and the glucose in the blood. The chemical reaction releases free electrons into the enzyme 56. This allows a current to flow between electrodes 30b and 30c as described in relation to FIG. 2.

When the fluid is placed on the fluid test strip 10, the fluid covers the enzyme 56 as well as the thermal connector 32. The thermal connector 32 transfers heat from the fluid to the resistor 14. The resistor 14 is then brought the same temperature as that of the fluid, as described previously in relation to FIG. 2.

Figure 4:
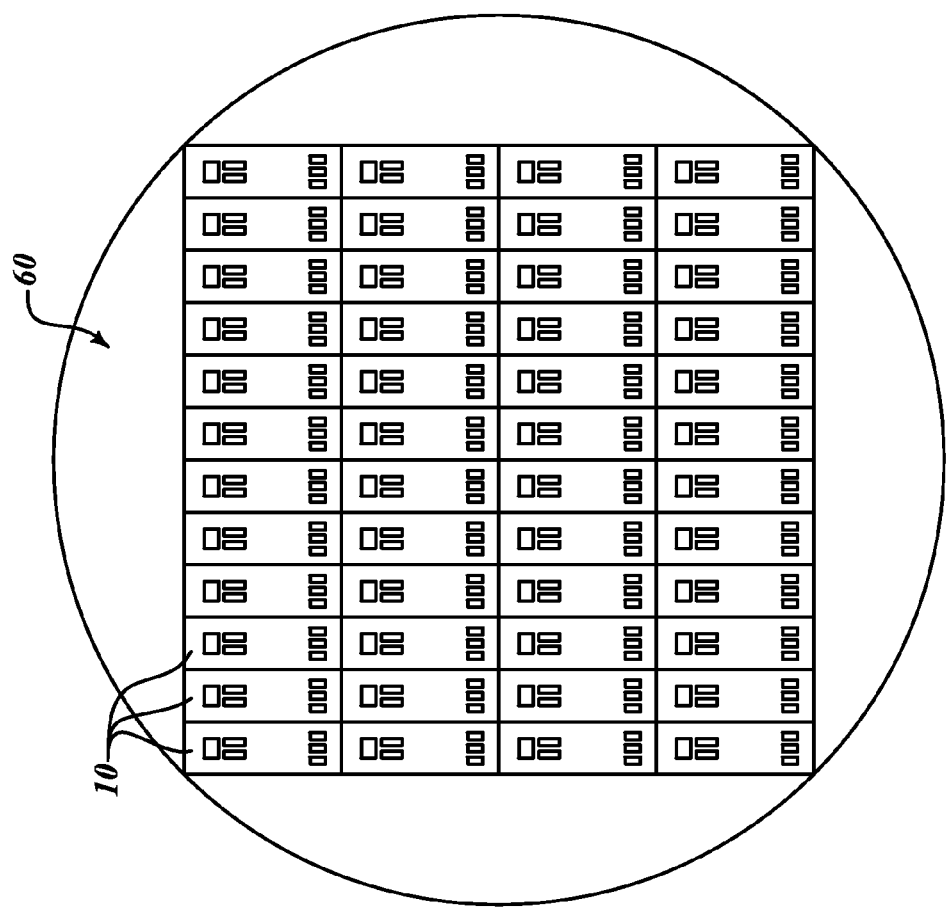
FIG. 4 is a top view of a wafer on which a plurality of fluid test strips are formed according to one embodiment.

FIG. 4 is a top view of a wafer 60 on which a plurality of fluid test strips 10 are formed according to one embodiment. The process steps described in relation to FIGS. 3A-3G are performed simultaneously on a wafer 60. Multiple fluid test strips 10 are formed simultaneously. Each of the process steps described in relation to FIGS. 3A-3G are performed on the entire wafer 60 so that many fluid test strips 10 can be manufactured in a relatively inexpensive manner at the same time. While on the wafer 60, the fluid test strips 10 are diced and separated from each other to form individual fluid test strips 10 which can be used in conjunction with a fluid test strip reader 16 as described previously.

Figure 5:
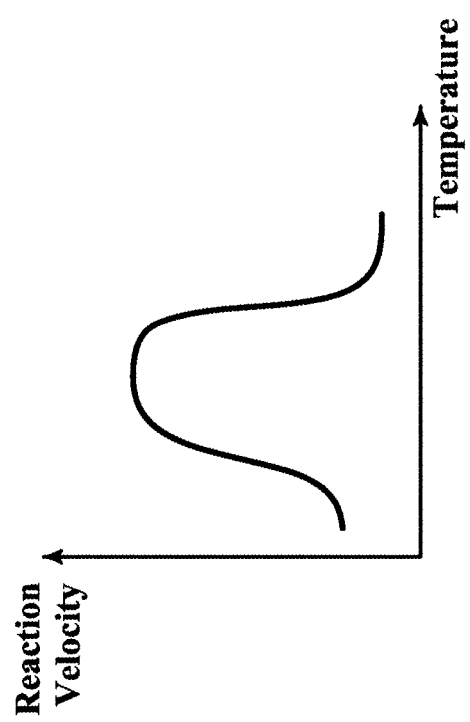
FIG. 5 is a graph of the reaction velocity between the enzyme and the analyte as a function of the temperature of the fluid according to one embodiment.

FIG. 5 is a plot of the reaction velocity between blood glucose and the enzyme glucose oxidase 56 versus temperature. The reaction velocity refers to the velocity of free charges in the enzyme that result from the reaction between glucose and the enzyme. As the reaction velocity increases so does the magnitude of the sensor current. As can be seen, the reaction velocity changes greatly with temperature and not in a linear fashion. By knowing the behavior of the reaction velocity with respect to changes in temperature, the test strip reader 16 can more accurately calculate the concentration of glucose in the blood.

Figure 6:
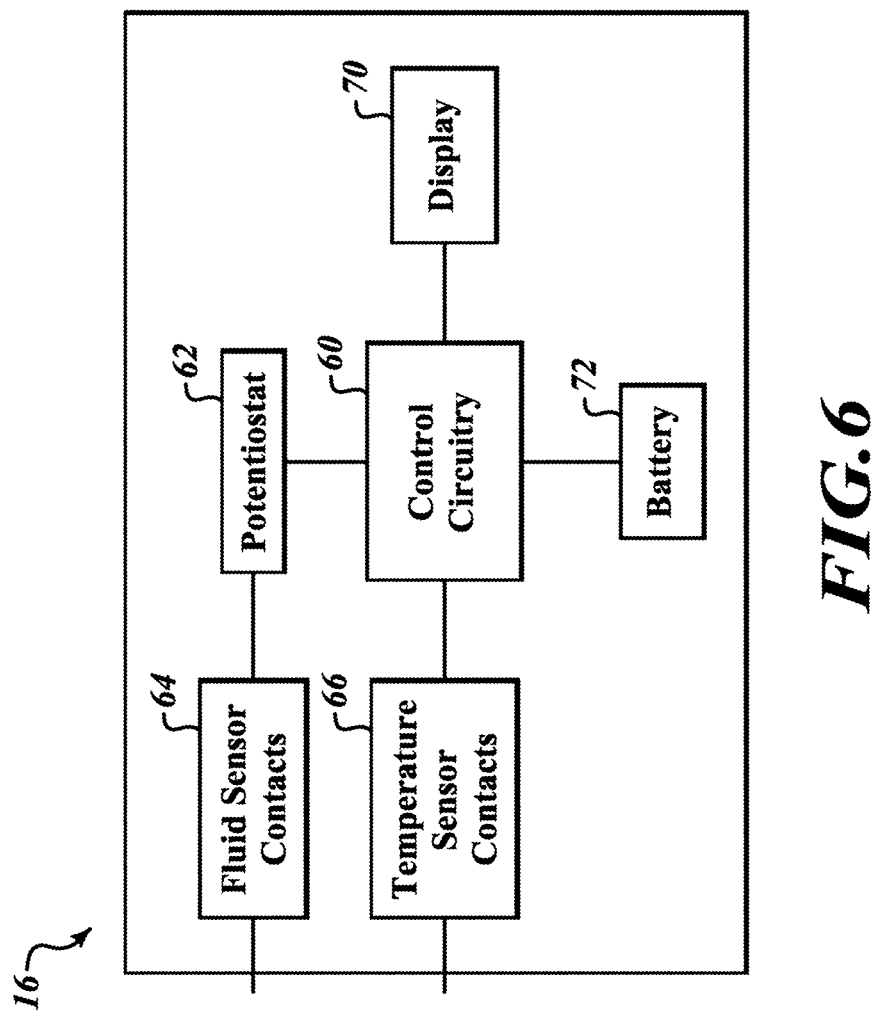
FIG. 6 is a block diagram of a fluid test strip reader according to one embodiment.

FIG. 6 is a block diagram of a fluid test strip reader 16 according to one embodiment. The fluid test strip reader 16 includes control circuitry 60. The control circuitry 60 can include one or more microcontrollers which control the other components of the fluid test strip reader 16 and calculate the concentration of the analyte in the fluid. The control circuitry 60 can also include memory circuits on which are stored tables or databases of values of concentration of the analyte for various values of temperature and sensor current.

A potentiostat 62 is coupled between the control circuitry 60 and fluid sensor contacts 64. The fluid sensor contacts 64 supply voltages to the contact pads 24b and 24c of the fluid test strip 10 as described in relation to FIG. 2. The fluid sensor contacts 64 also receive the sensor current from the contact pads 24b and 24c of the fluid test strip 10. The potentiostat 62 receives the sensor current from the fluid sensor contacts 64 and passes an amplified sensor signal to the control circuitry 60. The control circuitry 60 receives the amplified sensor signal and calculates the value of the concentration of the analyte in the fluid based in part on the amplified sensor signal.

Temperature sensor contacts 66 are also coupled to the control circuitry 60. A voltage is applied between the contact pads 24d and 24e of the fluid test strip 10 via the temperature sensor contacts 66. The temperature signal is returned from the temperature sensing resistor 14 to the temperature sensor contacts 66 to the control circuitry 60. The control circuitry 60 receives the temperature signal and calculates the concentration of the analyte in the fluid based on both the temperature signal and amplified sensor signal as described previously with relation to FIG. 2.

The fluid test strip reader 16 further includes a display 70 coupled to the control circuitry 60. The control circuitry 60 outputs on the display 70 the calculated value of the concentration of the analyte in the fluid. The display allows a technician to view the calculated concentration of the analyte. The fluid test strip reader 16 is powered by a battery 72 coupled to the control circuitry 60.

Figure 7:
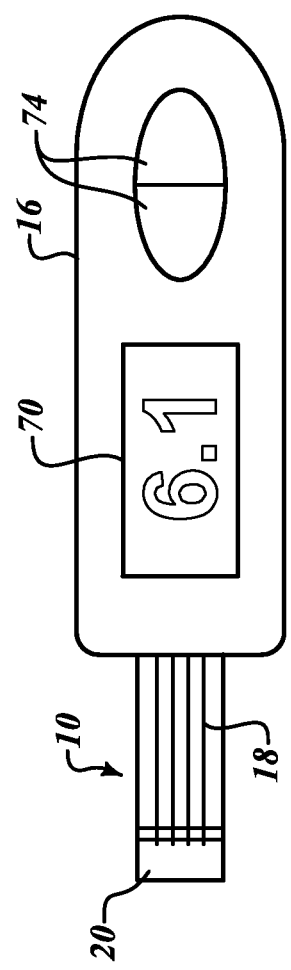
FIG. 7 is an illustration of a fluid test strip coupled to a fluid test strip reader according to one embodiment.

FIG. 7 is an illustration of a fluid test strip reader 16 having a fluid test strip 10 coupled thereto. The fluid receiving area 20 is visible on the left side of the fluid test strip 10. The electrodes and thermal conductors are not shown. The electrical connectors 18 connect the components in the fluid receiving area to contact pads 24a-24e which are coupled within the fluid test strip reader 16 and are not visible in FIG. 7. When the fluid test strip 10 is coupled to the fluid test strip reader 16 and fluid is placed in the fluid receiving area 20, a technician can operate buttons 74 of the fluid test strip reader 16 to initiate a measurement of the concentration of the analyte in the fluid. The fluid test strip reader 16 calculates the value of the concentration of the analyte based on both the temperature and the sensor current as described previously. The value of the concentration of the analyte in the fluid is then displayed on the display 70.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for forming a fluid sensor test strip, the method comprising:
    depositing a first dielectric material;
    etching a plurality of apertures in the first dielectric material;
    depositing a first metal layer on the first dielectric material and in the apertures to form a first and a second electrode and contact pads in the apertures;
    depositing a second metal layer in contact with the first metal layer, the second metal layer being of a material that has a resistance generally proportional to temperature;
    etching the second metal layer to define a temperature sensing resistor of the second metal layer;
    depositing a second dielectric material in the apertures adjacent the first and second metal layers; and
    depositing an enzyme on the first and second electrodes and extending from the first electrode to the second electrode, the enzyme configured to pass a sensor current between the first and the second electrodes indicative of a concentration of a test chemical in a test fluid when the test fluid is placed on the enzyme.

2. The method of claim 1 wherein the first metal layer is gold.

3. The method of claim 1 wherein the second metal layer is platinum.

4. The method of claim 1 wherein depositing the first metal layer includes forming at least one heat conducting electrode in at least one of the apertures, the temperature sensing resistor being thermally coupled to the heat conducting electrode.

5. The method of claim 1 wherein the first and second electrodes are respectively connected to first and second contact pads.

6. The method of claim 5 wherein the temperature sensing resistor is connected to third and fourth contact pads.

7. The method of claim 6 wherein a second current flowing between the third and fourth contact pads is indicative of a temperature of the test fluid.

8. The method of claim 1 wherein the first dielectric material is polyimide.

9. The method of claim 1 wherein top surface of the electrodes, top surfaces of the contact pads, and a top surface of the first dielectric material are planar with each other.

10. The method of claim 1 wherein the second dielectric material is an adhesive tape.

11. A method for forming a fluid sensor test strip, the method comprising:
   depositing a first dielectric material on a surface of a substrate;
   opening a plurality of apertures in the first dielectric material;
   forming a first and second electrodes and a plurality contact pads in the apertures by depositing a first metal layer on the first dielectric material and on the surface of the substrate in the apertures;
   depositing a second metal layer on the first dielectric material;
   etching the second metal layer to form a temperature sensing resistor connected between respective contact pads of the plurality of contact pads;
   depositing a second dielectric material on the first and second metal layers;
   removing the substrate from the first dielectric material, the plurality of contact pads, and the plurality of electrodes; and
   depositing an enzyme on the first and second electrodes, the enzyme configured to pass a sensor current between the first and the second electrodes indicative of a concentration of a test chemical in a test fluid when the test fluid is placed on the enzyme.

12. The method of claim 11 comprising attaching an adhesive substrate to the second dielectric material, a surface of the adhesive substrate being a backside of the fluid sensor test strip.

13. The method of claim 11 wherein a surface of the second dielectric material is a backside of the fluid sensor test strip.

14. The method of claim 11 wherein the first metal layer is gold.

15. The method of claim 11 wherein the second metal layer is platinum.

16. The method of claim 11 wherein surfaces of the first and second electrodes, the plurality of contact pads, and the first dielectric material are planar with each other.

17. A fluid sensor test strip comprising:
   a substrate;
   a first dielectric layer on the substrate;
   a second dielectric layer on the first dielectric layer, the second dielectric layer having a planar top surface;
   a temperature sensing resistor between the first and second dielectric layers;
   a plurality of apertures formed in the second dielectric layer;
   first and second electrodes and a plurality of contact pads each in a respective one of the plurality of apertures and having respective top surfaces planar with the top surface of the second dielectric layer; and
   an enzyme on the first and second electrodes, the enzyme configured to pass a sensor current between the first and second electrodes indicative of a concentration of a test chemical in a test fluid when the test fluid is placed on the enzyme.

18. The fluid sensor test strip of claim 17 comprising a plurality of metal lines between the first and the second dielectric layers, each metal line electrically connected to a respective one of the first and second electrodes and the temperature sensing resistor.

19. The fluid sensor test strip of claim 18 wherein the first and second electrodes and the plurality of metal lines are of a first metal.

20. The fluid sensor test strip of claim 19 wherein the temperature sensing resistor is of a second metal.

* * * * *